United States Patent
Dominick et al.

(10) Patent No.: US 10,586,016 B2
(45) Date of Patent: Mar. 10, 2020

(54) RELOCATING MEDICAL DATA

(71) Applicants: Lutz Dominick, Eggolsheim (DE); Vladyslav Ukis, Nürnberg (DE)

(72) Inventors: Lutz Dominick, Eggolsheim (DE); Vladyslav Ukis, Nürnberg (DE)

(73) Assignee: Siemens Healthcare GmbH, Erlangen (DE)

(*) Notice: Subject to any disclaimer, the term of this patent is extended or adjusted under 35 U.S.C. 154(b) by 662 days.

(21) Appl. No.: 15/094,590

(22) Filed: Apr. 8, 2016

(65) Prior Publication Data

US 2016/0300016 A1 Oct. 13, 2016

(30) Foreign Application Priority Data

Apr. 8, 2015 (EP) .................................... 15162767

(51) Int. Cl.
*G06F 19/00* (2018.01)
*H04L 29/06* (2006.01)
*G06F 16/21* (2019.01)
*G16B 50/00* (2019.01)
(Continued)

(52) U.S. Cl.
CPC .......... *G06F 19/321* (2013.01); *G06F 16/214* (2019.01); *G06F 19/324* (2013.01); *G16B 50/00* (2019.02); *H04L 51/046* (2013.01); *H04L 63/10* (2013.01); *H04L 67/1095* (2013.01);
(Continued)

(58) Field of Classification Search
CPC ............... G06F 17/3007; G06F 17/303; G06F 17/30244; G06F 19/28; G06F 19/32; G06F 19/321; G06F 19/324; G06F 19/3418; G06F 3/0647; G06F 11/1435; G06F 3/0605; G06F 3/0608; G06F 9/45533; G06F 16/214; G06Q 50/22; G06Q 50/24; G06Q 30/02; G16B 50/00; H04L 67/1095;
(Continued)

(56) References Cited

U.S. PATENT DOCUMENTS 7,111,061 B2  9/2006 Leighton et al.
7,778,972 B1  8/2010 Cormie et al.
(Continued)

FOREIGN PATENT DOCUMENTS

WO  WO0193538 A2  12/2001
WO  WO2010141460 A1  12/2010

OTHER PUBLICATIONS

Carter, Robert L., and Mark E Crovella. Dynamic server selection using bandwidth probing in wide-area networks. Boston University Computer Science Department, 1996.
(Continued)

*Primary Examiner* — Jungwon Chang
(74) *Attorney, Agent, or Firm* — Lempia Summerfield Katz LLC

(57) ABSTRACT

A method for relocating medical data in a computer network having a plurality of storage nodes connected via data transfer channels is provided. Technical conditions for relocating the medical data from a first storage node to a second storage node are determined. A relocation of the medical data is decided based on the technical conditions and a predetermined relocation plan. The medical data is automatically relocated from the first storage node to the second storage node via the transfer channel when a relocation of the medical data is decided.

25 Claims, 2 Drawing Sheets

(51) Int. Cl.
*H04L 29/08* (2006.01)
*H04L 12/58* (2006.01)

(52) U.S. Cl.
CPC .......... *H04L 67/1097* (2013.01); *H04L 67/12* (2013.01); *H04L 67/2814* (2013.01)

(58) Field of Classification Search
CPC . H04L 67/2814; H04L 67/1097; H04L 67/12; H04L 63/10; H04L 51/046
USPC .......................................... 711/165; 709/217
See application file for complete search history.

(56) References Cited

U.S. PATENT DOCUMENTS

| | | | | |
|---|---|---|---|---|
| 8,321,474 | B2* | 11/2012 | Schilken | G06Q 50/22 707/804 |
| 2002/0062225 | A1* | 5/2002 | Siperco | G06F 19/3418 705/2 |
| 2002/0198740 | A1* | 12/2002 | Roman | G06Q 30/02 705/3 |
| 2006/0242376 | A1* | 10/2006 | Tsuge | G06F 3/0605 711/165 |
| 2007/0011422 | A1* | 1/2007 | Srinivasan | G06F 17/30244 711/165 |
| 2007/0214016 | A1* | 9/2007 | Bennett | G06Q 50/24 705/3 |
| 2009/0150176 | A1* | 6/2009 | Gejdos | G06F 19/3418 705/2 |
| 2013/0110778 | A1* | 5/2013 | Taylor | G06F 11/1435 707/624 |
| 2014/0142984 | A1* | 5/2014 | Wright | G06F 19/321 705/3 |
| 2014/0324462 | A1* | 10/2014 | Beck | G06F 19/3418 705/3 |
| 2015/0302007 | A1* | 10/2015 | Sitka | G06F 17/303 707/602 |
| 2016/0162197 | A1* | 6/2016 | Effern | G06F 3/0608 711/154 |
| 2016/0188353 | A1* | 6/2016 | Shu | G06F 9/45533 718/1 |
| 2016/0196089 | A1* | 7/2016 | Gadre | G06F 3/0647 711/114 |

OTHER PUBLICATIONS

European Search Report for European Application No. 15 162 767.6-1952, dated Jul. 1, 2015.

Kayange, Daniel Sinkonde, et al. "A Practical Approach to Available Bandwidth Estimation Techniques (ABETs) for an Efficient Telemedicine Content Transport Network." International Journal of Scientific & Engineering Research 4.9 (2013).

\* cited by examiner

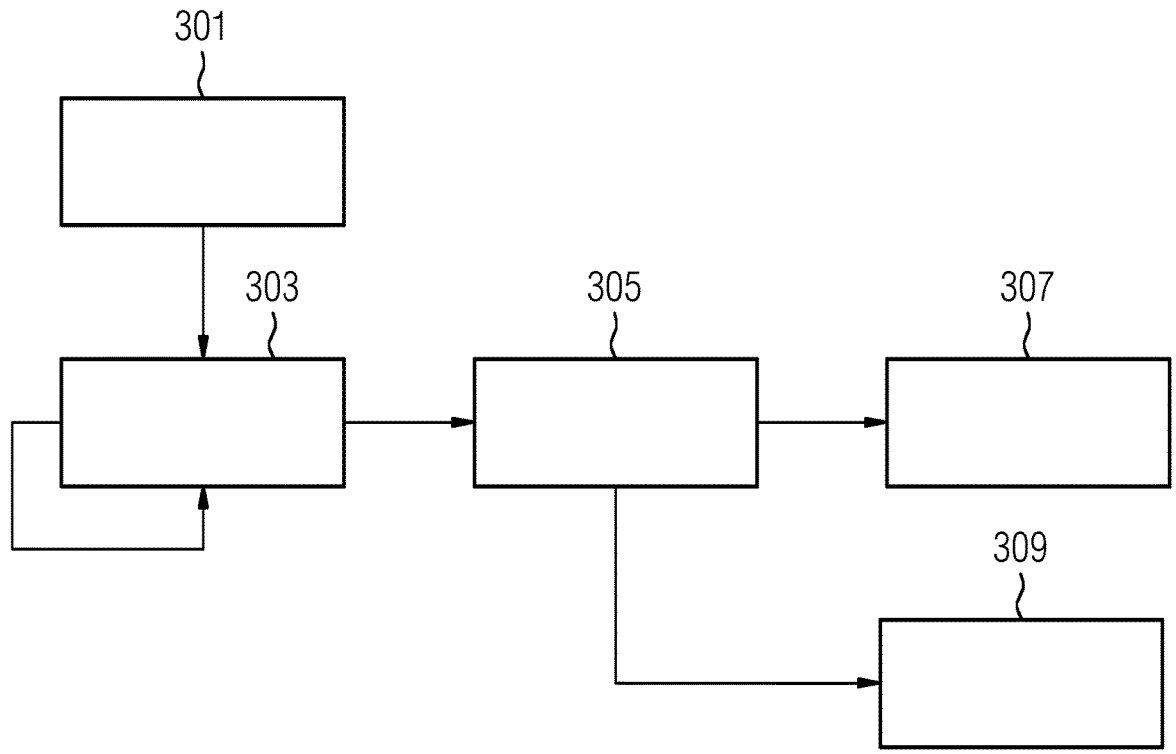
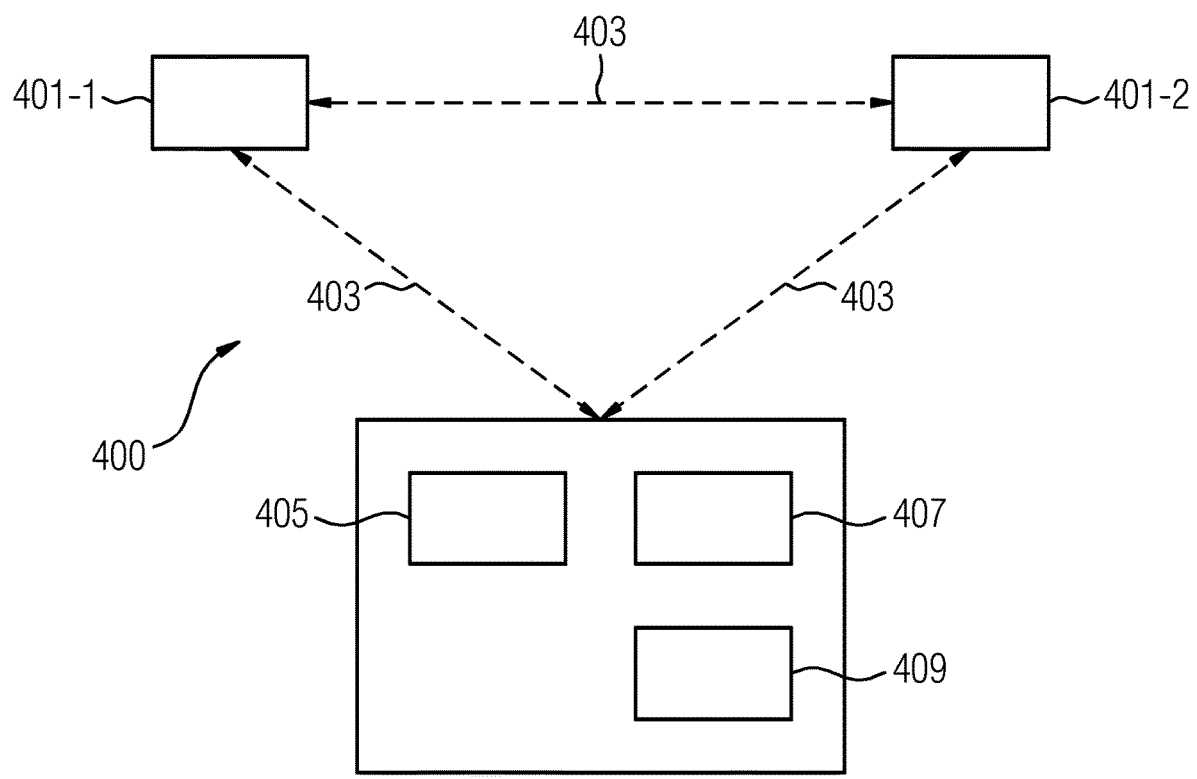

RELOCATING MEDICAL DATA

This application claims the benefit of EP 15162767.6, filed on Apr. 8, 2015, which is hereby incorporated by reference in its entirety.

BACKGROUND

The present embodiments relate to relocating medical data in a computer network having a number of storage nodes connected via data transfer channels.

In the medical imaging domain, hospitals use a high amount of structured and unstructured data, both from multi-vendor standards, like DICOM, and vendor specific standards. Cloud based approaches allow novel evaluations and calculations on the above data. There are main parameters that define aspects of a chosen cloud solution (e.g., operational pricing, transfer latency and data services). However, a cloud solution and a datacenter provider are chosen initially often based on a business strategy.

All these strategies assume some stability over time. Nevertheless, technical properties of datacenters vary over time. Novel technical solutions emerge and datacenters may compete on the marketplace. Accordingly, datacenters offer different technical services and pricings. Consequently, higher availability, faster transfer speed, or lower costs may be realized if the datacenter provider may be changed on the fly. A technical implication of not changing the provider may be the unavailability of dedicated services and higher latency so that a potential decrease in costs on-site is not realized.

Therefore, a hospital uses an online overview of technical capabilities and prices on the market place that fits to their own storage solution and business model. However, an automatic gathering of technical or pricing information from the Internet is often not possible. Consequently, automatically relocating of medical data is technically not feasible at reasonable efforts and costs. For the individual hospital, it is time-consuming and expensive to compare technical conditions, contracts, and pricings of a multitude of datacenter providers in order to provide technical standards, since this comparison requires a lot of manual work.

Sometimes, information on services and pricing is published in an unstructured way by datacenter providers, such as text on multiple web pages. Thus, relocation of the data to a different datacenter provider is a technically cumbersome procedure today. Therefore, a missing datacenter relocation or application integration option leads to technical blocking points and a vendor-lock-in situation, by which the hospital is bound to the datacenter provider. The vendor-lock-in is caused by the database technology and computer services provided by the datacenter.

SUMMARY AND DESCRIPTION

The scope of the present invention is defined solely by the appended claims and is not affected to any degree by the statements within this summary.

There is neither a prior art technical option to perform a relocation on a regular base nor a technical solution to do this on-the-fly. The present embodiments may obviate one or more of the drawbacks or limitations in the related art. For example, a fast and efficient relocation of medical data is provided.

According to a first aspect, a method for relocating medical data in a computer network having a plurality of (e.g., several) storage nodes connected via data transfer channels is provided. The method includes determining technical conditions for relocating the medical data from a first storage node to a second storage node, and deciding a relocation of the medical data based on the technical conditions and a predetermined relocation plan. The method also includes automatically relocating the medical data from the first storage node to the second storage node via the transfer channel if a relocation of the medical data is decided. This has the technical advantage that medical data may be transferred with low technical effort between datacenters. Medical data includes information that is obtained in a medical examination and may be used for digitally processing the information. Medical data may be stored in databases or files, such as Digital Imaging and Communications in Medicine (DICOM)-files. Each node may be based on a computer having a processor for processing data and a memory for storing data (e.g., a personal computer, a workstation or a terminal). A storage node is a node for digitally and permanently storing data (e.g., a cloud computer system, a server, or a datacenter). A transfer channel is a physical transmission medium such as a wire or a logical connection over a multiplexed medium such as a radio channel. The transfer channel is used to convey an information signal (e.g., a digital bit stream) from one node as a sender to another node as a receiver.

The technical conditions are technical parameters that affect the relocation of the medical data. Technical conditions may include the technical parameters of a bandwidth of the transfer channel, a duration of the relocation, an available storage space of the first storage node or the second storage node, a processing speed of the first storage node or the second storage node, and/or technical costs for relocating the medical data. Technical conditions may be based on use cases for the medical data that determine medical datasets requiring fast accessibility and medical datasets that may be retrieved later. Thus, medical datasets that may be retrieved later in the use case are relocated to a second storage node, whereas datasets requiring fast accessibility are kept at the local, first storage node.

However, the technical conditions may include other parameters relevant for relocating the medical data. The relocation plan, for example, determines which medical data may be transferred, at which time the medical data may be transferred, to which storage node the medical data may be transferred, and/or which the technical conditions for transferring the medical data should be.

In one embodiment of the method, the technical conditions for relocating the medical data are determined for a number of second storage nodes. In this embodiment, the technical advantage that the most suitable among a set of storage node may be chosen is achieved.

In a further embodiment of the method, the relocation plan is time-dependent. In this embodiment, the technical advantage that the medical data may be transferred differently in dependence on time (e.g., daytime or day of the week) is achieved.

In a further embodiment of the method, the technical conditions include a bandwidth of the transfer channel, a duration of the relocation, an available storage space of the first storage node or the second storage node, a processing speed of the first storage node or the second storage node, and/or technical costs for relocating the medical data. In this embodiment, the technical advantage that technical parameters that allow a fast relocation of the medical data are considered is achieved.

In a further embodiment of the method, the medical data are re-routed along data transfer channels in dependence of the relocation plan. In this embodiment, the technical advantage that the fast and reliable transfer channel may be chosen is achieved.

In an embodiment of the method, the technical conditions are determined by testing. In this embodiment, the technical advantage that up-to-date technical conditions may be determined (e.g., a bandwidth of the transfer channel or every other technical parameter may be tested by one of the storage nodes) is achieved.

In a further embodiment of the method, the medical data is fracked into a number of associated datasets. In this embodiment, the technical advantage that datasets that require fast access may be stored locally, while datasets that do not require fast access may be stored on a remote storage node is achieved. In general, every dataset may be stored independently in different storage nodes. Associated datasets include a logical link to other datasets so that the entire medical data may be reconstructed by following the logical link of the associated datasets.

In a further embodiment of the method, the address of a storage node, on which a particular dataset of the medical data currently resides, is stored in a database. In this embodiment, the technical advantage that all datasets may be accessed fast and reliably is achieved.

In one embodiment of the method, the address of a storage node, from which a particular dataset of the medical data has been transferred, is stored in a database. In this embodiment, the technical advantage that the course of medical datasets may be tracked is achieved.

In a further embodiment of the method, the relocation status of a particular dataset of the medical data is stored. In this embodiment, the technical advantage that an access to the dataset during transferal may be prevented is achieved. The relocation status includes information indicating the current process of the relocation (e.g., a pending relocation), an ongoing relocation, or a finished relocation of medical data.

In a further embodiment of the method, a request for accessing a dataset of the medical data is transmitted to an application that determines whether the dataset resides on the first storage node or the second storage node. In this embodiment, the technical advantage that a single access point is set up and all applications may retrieve the dataset in a transparent manner is achieved. The request is part of a request-response scheme that the nodes use to communicate to each other. The request-response scheme is a message exchange pattern in which a requestor sends a request message to a replier system that receives and processes the request, ultimately returning a message in response. An application is a computer program designed to carry out operations on the node.

In a further embodiment of the method, the application forwards the retrieved datasets to the requesting nodes. In this embodiment, the technical advantage that a single access point is set up and all applications may retrieve the dataset in a transparent manner is also achieved. The requesting node is the node that transmitted a request to the application residing in another node.

In an embodiment of the method, associated datasets are transferred in dependence on size or structure of the medical data. The structure of the medical data organizes the medical data in a way that the medical data may be used efficiently. Structures of the medical data may be, for example, arrays, lists, or graphs. In this embodiment, the technical advantage that access to the datasets may be optimized (e.g., by storing large datasets locally and small datasets in the remote storage node or by storing datasets of graphs locally and datasets of arrays or lists in the remote storage node) is achieved.

According to a second aspect, a device for relocating medical data in a computer network having several storage nodes connected via data transfer channels is provided. The device includes a determinator for determining technical parameters for relocating the medical data from a first storage node to a second storage node. The device also includes a decider for deciding a relocation of the medical data based on the technical conditions and a predetermined relocation plan. The device includes a relocator for automatically relocating the medical data from the first storage node to the second storage node via the transfer channel if a relocation of the medical data is decided. The device has the same technical advantages as the method according to the first aspect.

In one embodiment of the device, the determinator is configured to determine the technical conditions for relocating the medical data for a number of second storage nodes.

In a further embodiment of the device, the relocation plan is time-dependent.

In yet another embodiment of the device, the technical conditions include a bandwidth of the transfer channel, a duration of the relocation, an available storage space of the first storage node or the second storage node, a processing speed of the first storage node or the second storage node, and/or technical costs for relocating the medical data.

In a further embodiment of the device, the medical data is re-routable along data transfer channels in dependence of the relocation plan.

In a further embodiment of the device, the determinator is configured to determine the technical conditions by testing.

In a further embodiment of the device, the device includes a fracking device for fracking the medical data into a number of associated datasets.

In a further embodiment of the device, the device includes a database for storing the address of a storage node, on which a particular dataset of the medical data currently resides.

In one embodiment of the device, the device includes a database for storing the address of a storage node, from which a particular dataset of the medical data has been transferred.

In a further embodiment of the device, the device includes a database for storing the relocation status of a particular dataset of the medical data.

In a further embodiment of the device, the device includes a determinator for determining whether the dataset resides on the first storage node or the second storage node.

In an embodiment of the device, the determinator is configured to forward the retrieved datasets to the requesting nodes.

In a further embodiment of the device, associated datasets are transferrable in dependence on size or structure of the medical data.

According to a third aspect, a computer program product including a non-transitory computer-readable storage medium storing code instructions for executing the method according to the first aspect, if the code instructions are carried out on a computer, is provided. The computer program product has the same technical advantages as the method according to the first aspect.

BRIEF DESCRIPTION OF THE DRAWINGS

FIG. 3 shows an exemplary structure and basic execution sequence; and

FIG. 4 shows one embodiment of a device for relocating medical data in a computer network.

DETAILED DESCRIPTION

Figure 1:
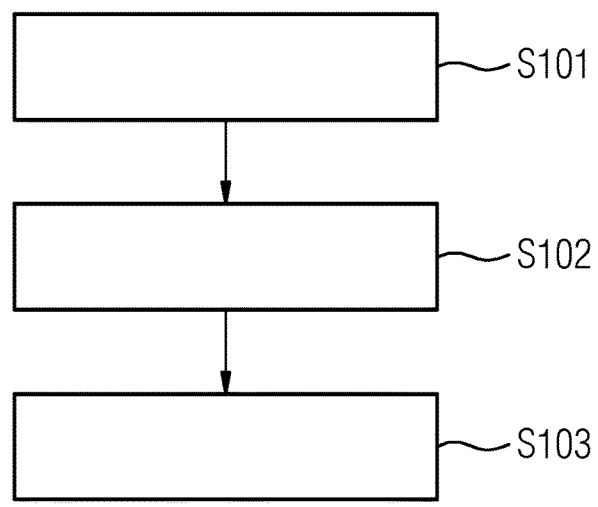
FIG. 1 shows a block diagram of one embodiment of a method.

FIG. 1 shows a block diagram of one embodiment of a method for relocating medical data in a computer network having several storage nodes connected via data transfer channels. The method includes the act S101 of determining technical conditions for relocating the medical data from a first storage node to a second storage node. In act S102, a relocation S102 of the medical data is decided based on the technical conditions and a predetermined relocation plan. In act S103, the medical data is relocated from the first storage node to the second storage node via the transfer channel if a relocation of the medical data is decided.

The relocation plan considers storage nodes and transfer channels (e.g., edges). Storage nodes are, for example, datacenters, on-premise or private clouds, cloud-on-the-box-solutions, and other storages for digitally storing medical data. Transfer channels (e.g., edges) include access points to storage nodes (e.g., datacenters) with dedicated bandwidth and latency or other network connections and hardware. The technical conditions include, for example, data sequences indicating a size of the medical data, a relocation time along the path given by one or more transfer channels, a domain data identification for the selected types of cohesive data fractals, or preferred execution hours. Cohesive provides that the datasets are logically linked so that each dataset points to a further dataset as part of the medical data. By cohesiveness, the first image, image text, and the patient quadruple data are available or directly accessible. In dependence on a particular use case, datasets that require fast access may be stored locally, whereas datasets to be processed later may be relocated.

Data fractals are based on a fractal tree index that is a generalization of a binary search tree in that a node may have more than two children. Unlike a B-tree, a Fractal Tree index has buffers at each node, which allow insertions, deletions, and other changes to be stored in intermediate locations.

The relocation plan may be created by online gathering and evaluating technical cloud data based on flexibly configurable strategies and information collection policies. The relocation plan defines which technical conditions are to be fulfilled for relocating the medical data.

Technical cloud data, for example, includes technical conditions defining the cloud in terms of a bandwidth of the transfer channel, a duration of the relocation, an available storage amount of the first storage node or the second storage node, a processing speed of the first storage node or the second storage node, and/or technical costs for relocating the medical data. In addition, non-technical parameters such as costs may be considered for deciding a relocation of the medical data. In case of damages or overload situations, the medical data may be re-routed through other network segments and transfer channels. Thus, cloud data relocation and migration and deployment of arbitrary enterprise data are supported.

Figure 2:
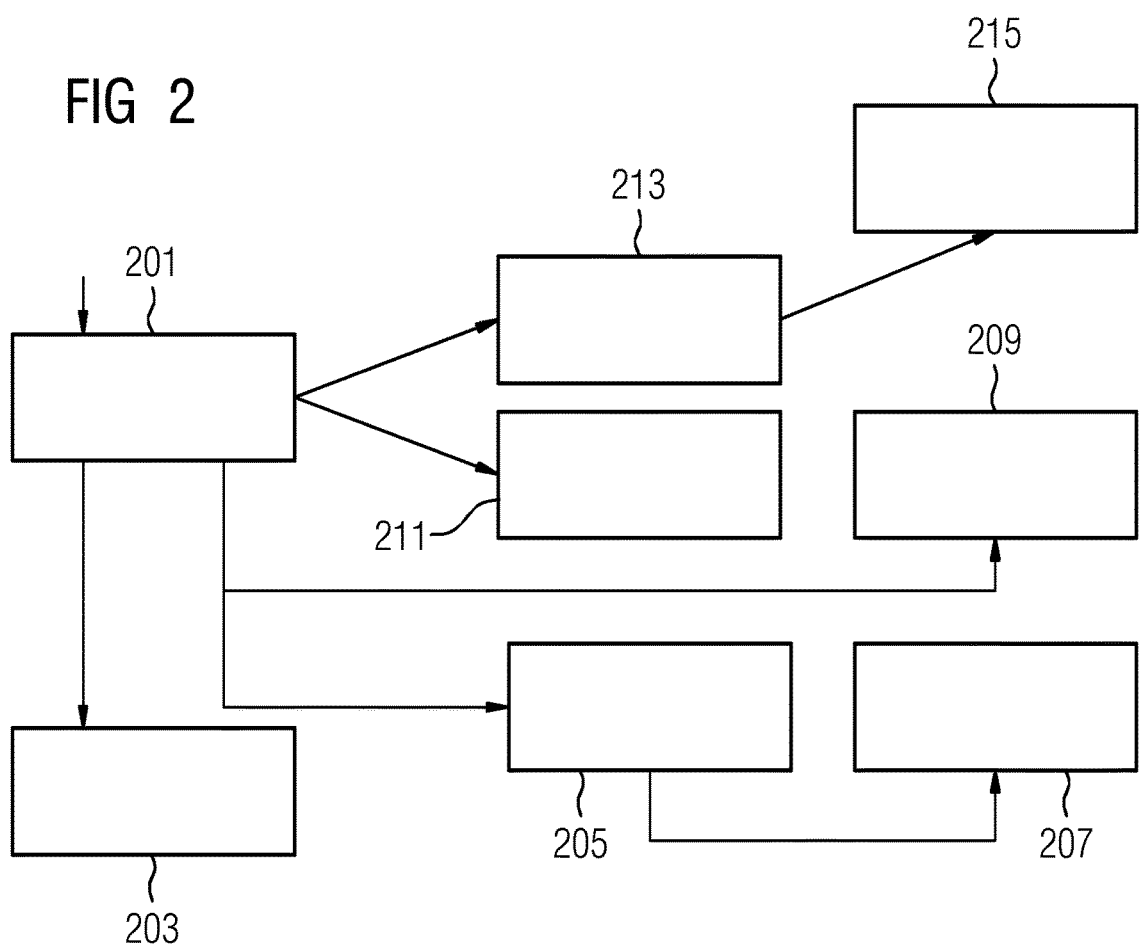
FIG. 2 shows an exemplary structure and basic interaction sequence of components.

FIG. 2 shows a structure and basic interaction sequence of components. The starting point is a user decision to generate up-to-date overview on technical conditions, pricing, and a possible relocation plan. The storage node is given by a datacenter or a cloud storage.

The user activates or triggers the JITRelocoAnalyzer component 201, which cooperates with a number of dedicated components in order to scan the technical conditions of a number of datacenters and involves the stored optimization strategies to create a suggestion with a datacenter to choose from. The JITRelocoAnalyzer 201 creates a relocation plan of data over time (e.g., the relocation plan contains one or multiple relocation sequences).

The JITRelocoAnalyzer 201 evaluates a relocation decision either automatically or on request by a user. The medical data to be relocated and the current datacenter are input. A result of the relocation decision is either to stay with the current datacenter or relocation with relocation data sequences. Then, data sequences run along a path from one datacenter to another over multiple transfer channels (e.g., edges).

A sequencer 203 with a sequence repository compares relocation plans and data sequences to running and historic data sequences in order to identify differences and to collect new data sequences.

A cost builder 205 with a compatible datacenter repository in combination with the datacenter scraper 207 search in the known and compatible datacenters for the technical conditions and cost listings for relocating the medical data on the Internet. Using additional tools in the datacenter scraper 207, other technical information may also be gathered. The scanned information is used to compare the current technical cost situation to the technical costs of other options (e.g., datacenters and on-premise/private solutions). The result is an option list of preferred options. In addition, different options for available bandwidths may be listed.

A PHI router 209 with a legal information repository checks the option list on how the medical data travel across or to a nation and if this travelling is in agreement according to national or international law.

A channelor 211 determines or measures latency or bandwidth as technical condition from or to datacenters and on-premise/private solutions. The channelor 211 creates a draft travelling layout plan with transfer channels and paths for the given medical data.

A time spacer 213 with a technical optimization strategy repository takes the medical data, the option list, and the bandwidths as inputs. Based on a corresponding technical strategies repository, the time spacer 213 calculates a relocation layout (e.g., which medical data are transferred to which datacenter, and a duration plan (chunks of the medical data in dependence on time and the time when the transferring is finished)). The time spacer 213 optimizes the relocation plan for the given medical data (e.g., what domain data to start with including business optimizations from the relocation board strategies like costs in dependence on time).

A relocation board 215 for business optimization strategies determines and applies optimization strategies that are used to create a correct plan for the given, overall business strategies. This denotes in which order the optimazation is performed and includes different strategies (e.g., costs in dependence on time or transferring novel medical data at first).

According to a plan, the medical data from a datacenter in South Carolina may be transferred to a datacenter in Texas. Technical conditions and costs for relocating the medical data in South Carolina from the datacenter to the datacenter in Texas are determined. For example, it is determined that the effort for virtual machines dropped by 50% with a double storage in the new datacenter in Texas. A transfer channel is rent as path from datacenter to datacenter for one day. All medical data is relocated to the datacenter (e.g., a cluster with Infiniband network inside) for immediate access by clinical applications.

The JITRelocoAnalyzer component 201 cooperates with an extensible number of dedicated and flexibly configurable components in order to automatically compare the own business to the pricings of datacenters and on-premise/private solutions and creates a plan for a technical solution that allows to profit from a new datacenter situation. The JITRelocoAnalyzer component 201 or equivalent applications may use a user interface to interact with an administrator and to give access to implemented capabilities.

This method enables the hospital to technically and automatically detect opportunities to involve faster and cheaper datacenters in storing medical data and to create the technical relocation plans to harvest the opportunity with a pre-calculated return-on-invest rate. The method gives a generic technical framework or application to compare the technical aspects and pricing and of datacenters based on relocation plans and business strategies.

FIG. 3 shows a structure and basic execution sequence that performs automatic and transparent data relocation on-the-fly with maximized availability and performance flexibly over multiple datacenters or other storage solutions for redeployment of arbitrary medical data with fully configurable strategies for business and domain data alignment based on associated datasets of the medical data (e.g., cohesive data fractals). Cohesive data fractals include a number of logically associated datasets based on a fractal tree index.

Medical data may be DICOM data. The medical data may be transferred by pull or push services. Procedure steps, studies, or reports may be exchanged based on a multi-vendor DICOM standard. The standard provides domain entities, service types, and provider and consumer classes. For the completeness of a transfer, all data is transferred. Other aspects are subject of a concrete implementation (e.g., a storage of DICOM data, an optimized transfer speed, and a providing and updating of additional medical and non-medical data based on the use case that is running inside the medical application or service).

The clue of arbitrary access and relocation of medical data in terms of cohesive data fractals is the ability to guarantee a degree of partitioning of the medical data in associated datasets that allows identifying a permanent or transient closure or boundary around the requested data such that the loaded amount of medical data is consistent. Nevertheless, the amount is smaller than all requested data. While cohesiveness in terms of the use case is to be provided, entity integrity (e.g., as of relational databases) and completeness may be considered later, also depending on the use case.

A clinical application 301 requests medical data for a use case. The user performs interactive use cases in an application that requests data.

Each application is connected to a single online shielding component 303, which is a single migration-independent access point of service for the application. The online shielding component 303 knows the current datacenter and checks if data relocation has an advantage for handling use cases, or another or no relocation sequence has been decided (e.g., by the administrator) and uses the new datacenter. By contacting the online shielding component 303, the application is unaware from which datacenter the data request is fulfilled.

A multi cloud Relocat component 305 processes both the data request and full relocation plans and performs the fracking of medical data into cohesive data fractals based on the strategies in the fractals repository. The multi cloud Relocat component 305 knows the structure of the domain data in the cloud storage types. The multi cloud Relocat component 305 relocates medical data upon request between datacenters and forwards the requested medical data to applications.

An internal load monitor optimizes if associated datasets, as dedicated cohesive data fractals, should be retrieved from the former datacenter (e.g., when traffic to the new datacenter uses bandwidth excessively). The multi cloud Relocat component 305 also triggers to re-register medical data to preserve hyperlinks for representational state transfer (REST) information, while indexes are updated by the data storage, when new data arrives.

The datacenter provides dedicated data services 307 and storage types. Relocation of two datacenters with the identical cloud technology relocates and updates to indexes and REST information.

A cloud-RESTer component 309 is a data and resource re-registration service. This form of updates to REST information inside the newly arrived data is used if the data is localized in the new datacenter.

All medical data in the application user interface is cohesive for a given use case, so the cohesiveness may be re-used for processes such as, for example, data relocation. It is to be determined if a data request is received from an interactive use case or not, in order to optimize the handling of cohesive data. DICOM data and related information may always be partitioned into cohesive fractals in dependence on the application use case. Large data approaches enable stronger partitioning in the data storages with faster access times. Therefore, large medical data supports the benefits from cohesive data fractals driven by use cases.

An example is medical data for dose management for scanners. Cohesive data fractals allow faster load times and thereby also focused and faster relocation times for interactive use cases. When performed in the background without interactive use cases, the cohesive data fractals may get larger and look like a DICOM query of a full study for a patient. A next act may be a relocation of the priors, which gives an optimization strategy for completeness first, while interactive use cases are to optimize on the first series or image.

As an example use case, the cohesive dataset enables displaying a first image of an image stack of a series so that only the first image, image text, and the patient quadruple data are available. The multi cloud Relocat component 305 and online shielding component 303 enable a data relocator of cohesive data fractals that allows to optimize either for interactive use cases or background migration.

Reading applications may use the online shielding component 303 to automatically load and store medical data transparently to the designated datacenter. The multi cloud Relocat component 305 automatically relocates medical data that adheres to the requested data.

Administrative applications use the online shielding component 305 to automatically relocate full archives, which may require dedicated optimization strategies that are available in the fractals repository of the multi cloud Relocat component 305.

This enables to directly support the use cases with cohesive data fractals and to give a novel implementation of the CAP theorem that it is impossible for a distributed computer system to simultaneously provide all three of consistency, availability and partition tolerance.

For the sake of performance, availability is focusing on the use case, while partitioning is guided by the cohesive data fractals aligned with the known structure of the domain data. Consistency is provided with the online shielding component 303 to provide all running use cases with a common view on all available data, while some unknown amount of relocation is running in the background. The CAP theorem shows that the approach will work.

The starting point is the generic multi cloud Relocat component 305 that relocates the cohesive data fractals of medical data between two arbitrary datacenters. The multi cloud Relocat component 305 provides that, even if data relocation is ongoing, online access to the medical data is granted to the applications or other use cases. Multiple relocations sequences from or to the same or different datacenters may be active at the same time.

Starting with the use case of a clinical application, the data request is transmitted first to the online shielding component 303, which manages running data relocations, is able to request new data relocations, and functions as the data end point that is visible to applications and delivers the requested data. Internally, the online shielding component 303 cooperates with an instance of the multi cloud Relocat component 305 that knows the datacenter in which the actual medical data currently resides. In addition, the multi cloud Relocat component 305 knows from where the actual medical data were transmitted and if the relocation is still running.

FIG. 4 shows one embodiment of a device for relocating medical data in a computer network 400 having several storage nodes 401 connected via data transfer channels 403. The device includes a determinator 405 for determining technical conditions for relocating the medical data from a first storage node 401-1 to a second storage node 401-2. The device also includes a decider 407 for deciding a relocation of the medical data based on the technical conditions and a predetermined relocation plan. The device includes a relocator 409 for automatically relocating the medical data from the first storage node 401-1 to the second storage node 401-2 via the transfer channel 403 if a relocation of the medical data is decided.

The determinator 405, the decider 407 and the relocator 409 may be implemented by hardware circuits or software programs that run on a computer with a memory and a storage.

The advantage that a planned background relocation or on-the-fly migration of medical data is possible in parallel to the regular clinical workflows is achieved. The ability to relocate and migrate medical data technically mitigates a vendor-lock-in by which the hospital is bound to a particular provider of the datacenter. The hospital is independent from the future structure of the physical layouts of the datacenter and datacenter provider market (e.g., including on-premise/ private cloud options or products like cloud-on-the-box).

Applications such as reading applications and administrator applications show the name of the data storage explicitly in the user interface. A changed datacenter name with cloud enabled medical application is also displayed in the user interface. Administrator applications show the relocation datacenters and editors for the fractal data handling strategies explicitly.

The method is able to handle an unlimited number of medical data or datasets and provides a rapid import and retrieval of medical data. In addition, a real-time processing and immediate query on even new imported medical data is possible Small response times for complex queries and handling of multiple concurrent queries are provided. Dedicated queries on types of data, like numbers, texts, and images may be performed.

All features discussed in terms of method acts may be realized by one or more devices adapted to perform the corresponding method acts. The scope of the invention is defined by the claims and is not restricted by special features discussed in the description or shown in the figures. All features discussed with respect to different embodiments may be combined variously and independently in order to simultaneously realize technical effect.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for relocating medical data in a computer network having a plurality of storage nodes connected via data transfer channels, the method comprising:
   determining technical conditions for relocating the medical data from a first storage node of the plurality of storage nodes to a second storage node of the plurality of storage nodes;
   determining a relocation of the medical data based on the determined technical conditions and a predetermined relocation plan;
   fracking the medical data into one or more associated datasets based on a required access speed, wherein the one or more associated datasets include a logical link between the one or more associated datasets such that the medical data is reconstructable by following the logical link; and
   automatically relocating the associated datasets from the first storage node to the second storage node via one of the data transfer channels when the relocation of the medical data is determined,
   wherein the technical conditions comprise technical costs for relocating the medical data, the technical costs including pricing for relocating the medical data.

2. The method of claim 1, wherein the technical conditions for relocating the medical data are determined for a number of storage nodes of the plurality of storage nodes.

3. The method of claim 1, wherein the predetermined relocation plan is time-dependent.

4. The method of claim 1, wherein the technical conditions further comprise a bandwidth of the transfer channel, a duration of the relocation, an available storage space of the first storage node or the second storage node, a processing speed of the first storage node or the second storage node, or any combination thereof.

5. The method of claim 1, wherein the medical data is re-routed along data transfer channels in dependence of the predetermined relocation plan.

6. The method of claim 1, wherein determining the technical conditions comprises determining the technical conditions by testing by one or more storage nodes of the plurality of storage nodes.

7. The method of claim 1, wherein an address of a storage node of the plurality of storage nodes, on which a particular dataset of the medical data currently resides, is stored in a database.

8. The method of claim 1, wherein an address of a storage node of the plurality of storage nodes, from which a particular dataset of the medical data has been transferred, is stored in a database.

9. The method of claim 1, further comprising storing a relocation status of a particular dataset of the medical data.

10. The method of claim 1, further comprising transmitting a request for accessing a dataset of the medical data to an application that determines whether the dataset resides on the first storage node or the second storage node.

11. The method of claim 10, further comprising forwarding, by the application, the retrieved datasets to requesting nodes.

12. The method of claim 1, wherein associated datasets are transferred in dependence on size or structure of the medical data.

13. A system for relocating medical data in a computer network, the system comprising:
a data transfer channel;
a plurality of storage nodes connected via the data transfer channel;
a device configured to:
determine technical conditions for relocating the medical data from a first storage node of the plurality of storage nodes to a second storage node of the plurality of storage nodes;
decide a relocation of the medical data based on the determined technical conditions and a predetermined relocation plan;
frack the medical data into one or more associated datasets based on a required access speed, wherein the one or more associated datasets include a logical link between the one or more associated datasets such that the medical data may be reconstructed by following the logical link; and
automatically relocate the medical data from the first storage node to the second storage node via the data transfer channel when the relocation of the medical data is decided,
wherein the technical conditions comprise technical costs for relocating the medical data, the technical costs including pricing for relocating the medical data.

14. The system of claim 13, wherein the device is configured to determine the technical conditions for relocating the medical data for a number of storage nodes of the plurality of storage nodes.

15. The system of claim 13, wherein the relocation plan is time-dependent.

16. The system of claim 13, wherein the technical conditions further comprise a bandwidth of the transfer channel, a duration of the relocation, an available storage space of the first storage node or the second storage node, a processing speed of the first storage node or the second storage node, or any combination thereof.

17. The system of claim 13, wherein the medical data is re-routable along data transfer channels in dependence of the predetermined relocation plan.

18. The system of claim 13, wherein one or more storage nodes of the plurality of storage nodes are configured to determine the technical conditions by testing.

19. The system of claim 13, further comprising a database configured to store an address of a storage node of the plurality of storage nodes, on which a particular dataset of the medical data currently resides.

20. The system of claim 13, further comprising a database configured to store an address of a storage node of the plurality of storage nodes, from which a particular dataset of the medical data has been transferred.

21. The system of claim 13, further comprising a database configured to store a relocation status of a particular dataset of the medical data.

22. The system of claim 13, wherein the device is configured to determine whether the dataset resides on the first storage node or the second storage node.

23. The system according to claim 22, wherein the device is configured to forward the retrieved datasets to the requesting nodes.

24. The system of claim 13, wherein associated datasets are transferrable in dependence on size or structure of the medical data.

25. In a non-transitory computer-readable storage medium storing code instructions executable by a computer to relocate medical data in a computer network having a plurality of storage nodes connected via data transfer channels, the instructions comprising:
determining technical conditions for relocating the medical data from a first storage node of the plurality of storage nodes to a second storage node of the plurality of storage nodes;
determining a relocation of the medical data based on the determined technical conditions and a predetermined relocation plan;
fracking the medical data into one or more associated datasets based on a required access speed, wherein the one or more associated datasets include a logical link between the one or more associated datasets such that the medical data is reconstructable by following the logical link; and
automatically relocating the medical data from the first storage node to the second storage node via a transfer channel when the relocation of the medical data is determined,
wherein the technical conditions comprise technical costs for relocating the medical data, the technical costs including pricing for relocating the medical data.

* * * * *